(12) United States Patent
Fasulka

(10) Patent No.: US 7,807,108 B2
(45) Date of Patent: Oct. 5, 2010

(54) APPARATUS FOR RECEIVING BIOLOGICAL SPECIMENS

(75) Inventor: Robert Fasulka, Westwood, NJ (US)

(73) Assignee: Leica Microsystems CMS GmbH, Wetzlar (DE)

( * ) Notice: Subject to any disclaimer, the term of this patent is extended or adjusted under 35 U.S.C. 154(b) by 995 days.

(21) Appl. No.: 11/532,841

(22) Filed: Sep. 18, 2006

(65) Prior Publication Data

US 2008/0069737 A1 Mar. 20, 2008

(51) Int. Cl.
B01L 3/00 (2006.01)
(52) U.S. Cl. ............... 422/102; 422/99; 422/104
(58) Field of Classification Search ............ 422/102; 435/4, 30, 287.1
See application file for complete search history.

(56) References Cited

U.S. PATENT DOCUMENTS

| 5,972,694 A * | 10/1999 | Mathus | 435/288.4 |
|---|---|---|---|
| 2003/0180941 A1* | 9/2003 | Schutze | 435/297.5 |
| 2004/0203174 A1* | 10/2004 | Jones et al. | 436/180 |
| 2006/0121298 A1 | 6/2006 | Wittke et al. | |
| 2007/0031816 A1* | 2/2007 | Schuetze et al. | 435/4 |

FOREIGN PATENT DOCUMENTS

| DE | 100 43 506 | 12/2001 |
|---|---|---|
| DE | 102 34 755 | 2/2004 |
| WO | WO-0035583 | 6/2000 |
| WO | WO-2004019007 | 3/2004 |
| WO | WO-2005057178 | 6/2005 |
| WO | WO-2005057179 | 6/2005 |
| WO | WO 2006/024392 * | 3/2006 |
| WO | WO-2006/024392 | 3/2006 |

OTHER PUBLICATIONS

G. Isenberg; W. Bielser; W. Meier-Ruge; E. Remy, cell surgery by laser microdissection: a preparative method, Journal of Microscopy, vol. 107, May 1976, pp. 19-24.

* cited by examiner

Primary Examiner—Robert J Hill, Jr.
Assistant Examiner—Dwan A Gerido
(74) Attorney, Agent, or Firm—Leydig, Voit & Mayer, Ltd.

(57) ABSTRACT

An apparatus for receiving biological specimens, the apparatus being introducible into a laser microdissection device for laser microdissection of a biological specimen, includes a first element having a first opening extending from a first side to a second side of the first element. A second element is provided having a second opening extending from a third side to a fourth side of the second element. The second opening is closed at the third side. The second element is disposed relative to the first element so that the first opening is aligned with the second opening. A layer is disposed between the first and second elements, the layer being designed to receive the biological specimen thereon and being capable of being cut through by laser light in a laser microdissection operation so that a portion of the biological specimen is received in the second opening so as to remain inside the apparatus.

35 Claims, 9 Drawing Sheets

APPARATUS FOR RECEIVING BIOLOGICAL SPECIMENS

The present invention relates to an apparatus for receiving biological specimens. The apparatus is introducible into a laser microdissection device for laser microdissection of at least one biological specimen. The apparatus encompasses a substantially plate-shaped first element, a substantially plate-shaped second element, and a layer. The first element comprises at least one opening or cutout that extends from a first side of the element to a second side of the element. The second element comprises at least one opening or cutout that extends from a first side of the second element into the second element, this opening being closed off or delimited with respect to a second side, located opposite the first side, of the second element. A base or a chamber is thereby formed. For many applications, it may be useful for the first and/or second element to comprise from two to 96 openings. The layer is embodied in such a way that it can be at least partly cut through by means of laser light. The present invention furthermore relates to a use of an apparatus for receiving biological specimens, and to a method for laser microdissection of at least one biological specimen.

BACKGROUND

In the field of biology and medicine, "microdissection" refers to a method with which a small piece can be cut out from a generally flat sample or biological specimen (for example, cells, a cell agglomeration, or a tissue section) using a narrow, focused laser beam. The cut-out piece is, as a rule, physically separated from the biological specimen and is thus available for further biological or medical (e.g. histological) investigations. The manner in which the sample is prepared depends, inter alia, on the laser microdissection method with which processing of the sample is to be performed.

DE 102 34 755 A1, which is hereby incorporated by reference herein, describes a carrier apparatus for a biological sample or specimen that is cuttable by means of laser microdissection. This carrier apparatus is a Petri dish in which, however, the base is embodied in the form of a self-supporting laser-light-absorbing film, the sample or specimen being arranged on the film. The laser microdissection device provided therein encompasses a transmitted-light microscope having an X-Y stage on which the carrier apparatus with the specimen is arranged. Arranged below the specimen is a collection receptacle for collecting the cut-out sample region.

A laser beam proceeds from a UV laser and is coupled into an incident illumination beam path. The laser beam proceeds via an optical system to an objective that focuses the laser beam onto the sample. The laser beam is movable relative to a biological specimen or to the film. Also, for example, a laser scanning device is arranged in the illumination beam path, with which device the laser beam is deflected. Alternatively, the microscope stage is moved relative to the laser beam.

A method of this kind has already been described in the article "Cell surgery by laser microdissection: a preparative method," G. Isenberg, W. Bielser, W. Meier-Ruge, E. Remy, Journal of Microscopy, Vol. 107, May 1976, pp. 19-24. Here a focused laser beam of a pulsed UV laser is directed from above onto a (preferably biological) sample, and the focused laser beam is moved around a sample region of interest along a continuous cut line. The sample region of interest is thereby completely detached from its surroundings and falls into a collection apparatus. In DE 102 34 755 A1, a collection apparatus, into which the cut-out specimen portion along with a piece of film falls, is arranged below the carrier apparatus.

A more recent method and an apparatus for laser microdissection are described by DE 100 43 506 C1. Here a focused laser beam is directed from above onto a (preferably biological) sample. In a first step, the focused laser beam is moved around a sample region of interest along an open cut line that largely encloses the sample region of interest; there remains, between the beginning and end of the cut line, a stable web that continues to connect the sample region of interest to the surrounding specimen. In a second step, the web is cut through with a single focused laser pulse directed onto the web, the cut width having previously been adapted to the width of the web, i.e. enlarged. The sample region of interest is completely detached from its surroundings by the last cutting laser pulse, and falls downward. As compared with the method recited previously, this method has the advantage that toward the end of the cutting operation it prevents the almost-cut-out sample region from swinging away or rotating.

WO 2006/024392 A2, which is hereby incorporated by reference herein, describes a carrier apparatus for laser microdissection that is usable in an inverted microscope. Here the biological specimen is located on a (generally conventional) specimen slide, and the laser beam used for laser microdissection is focused from below, i.e. through the specimen slide, onto the biological specimen, and the region of interest is correspondingly cut out. For separation of the selected specimen region, the latter is then catapulted away from the specimen slide, with the aid of an additional laser pulse, to a collection apparatus arranged above the specimen slide and arranged movably in its position relative to the specimen slide. This separation procedure is also referred to as a laser catapulting method.

SUMMARY

The previous fields of application of laser microdissection encompassed the selection of cells from histological sections, e.g. in molecular pathology, cell biology, and neurological research, in other words cells mainly from biological specimens that are no longer living. An increasing application demand also exists, however, for selecting cells from a culture or agglomeration of living cells. It is important in this context, however, that the living cells or biological specimens not be contaminated by the external environment, so that no fungi or bacteria can overgrow the specimens that actually need to be investigated or processed. It can furthermore be important as well for the biological specimens to be present in suitable environmental conditions, the principal factors here being (in addition to an appropriate nutrient solution) the presence of a suitable definable temperature and suitable atmospheric conditions. It is therefore desirable if the specimens can be processed by laser microdissection in a sterile environment, and sealed off from the external environment. If that should not be the case, contamination of the laser microdissection device can occur because the carrier apparatus also comes into contact with culture medium in the region of its frame or lower side, so that cells or fungi can likewise become established there. In terms of the investigation of disease-causing agents, the result is therefore not only a handling problem but also a hygiene problem.

An object of the present invention is therefore to provide an apparatus for receiving biological specimens and a method for laser microdissection of at least one biological specimen, with which one the one hand living biological specimens can be processed using the laser microdissection method, and which on the other hand can be embodied in a manner closed off from the environment.

In an embodiment, the present invention provides an apparatus for receiving biological specimens, the apparatus being introducible into a laser microdissection device for laser microdissection of a biological specimen. The apparatus includes:

a first element including a first opening extending from a first side to a second side of the first element;

a second element including a second opening extending from a third side to a fourth side of the second element, the second opening being closed at the third side, the second element being disposed relative to the first element so that the first opening is aligned with the second opening; and a layer disposed between the first and second elements, the layer being configured to receive the biological specimen thereon and being capable of being cut through by laser light in a laser microdissection operation so that a portion of the biological specimen is receivable in the second opening so as to remain inside the apparatus.

In another embodiment, the present invention provides a method for laser microdissection of a biological specimen. The method includes:

providing an apparatus for receiving the biological specimen, the apparatus comprising:

a substantially plate-shaped first element including a first opening extending from a first side to a second side of the first element;

a substantially plate-shaped second element including a second opening extending from a third side to a fourth side of the second element, the second opening being closed at the third side, the second element being disposed relative to the first element so that the first opening is aligned with the second opening; and a layer disposed between the first and second elements, the layer being configured to receive the biological specimen thereon and being capable of being cut through by laser light in a laser microdissection operation so that a portion of the biological specimen is receivable in the second opening so as to remain inside the apparatus;

introducing the biological specimen into the apparatus;

introducing the apparatus into a laser microdissection device; and performing the laser microdissection operation so as to cut through the layer so that the portion of the biological specimen is received in the second opening so as to remain inside the apparatus.

BRIEF DESCRIPTION OF THE DRAWINGS

There are various ways of embodying and refining the teaching of the present invention. The reader is referred to the explanation below of exemplifying embodiments of the invention with reference to the drawings. In the drawings, schematically in each case.

In the Figures, identical or similar components are identified by the same reference characters.

DETAILED DESCRIPTION

Figure 1:
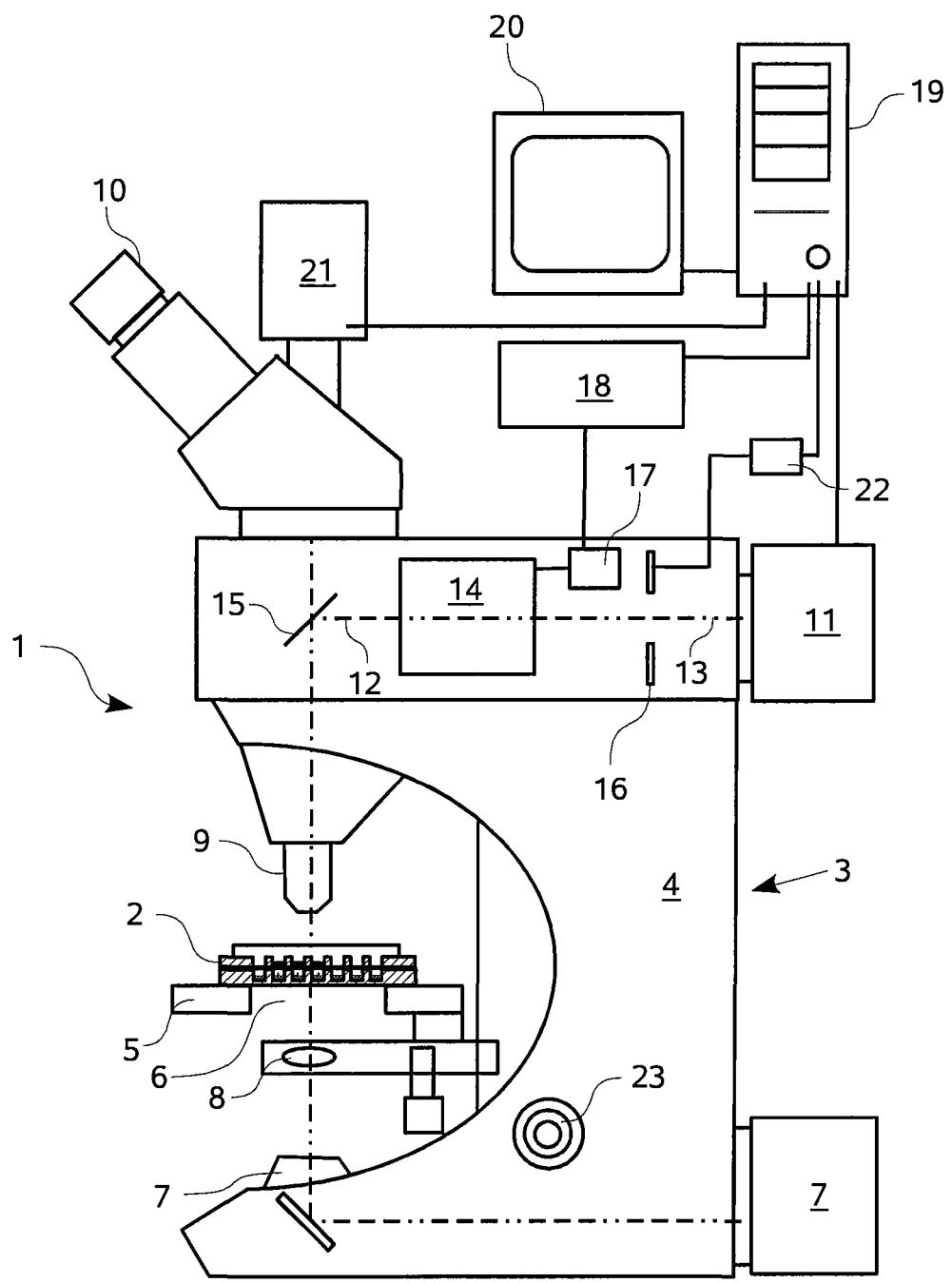
FIG. 1 shows a laser microdissection device adapted in an upright microscope, in which device is introduced a first exemplifying embodiment of an apparatus according to the present invention for receiving biological specimens.

According to the present invention, the at least one biological specimen is arrangeable on the layer in the apparatus in such a way that it remains inside the apparatus during and after a laser microdissection operation. As a rule, the laser microdissection operation is performed on the layer, a portion of the biological specimen being cut out and falling in an opening of the second element.

An "opening" could encompass for purposes of the present invention, for example, an orifice, a cutout, and/or a blind hole. The term "align" for purposes of the present invention means in particular that a longitudinal axis or a central axial course of an opening of the first element comes substantially into congruence with a longitudinal axis or a central axial course of an opening of the second element. In addition, it is not absolutely necessary for the diameter or dimension of the opening of the first element to be of the same size as the opening of the second element. It might be useful, for example, for the opening of the second element to have a larger diameter than the opening of the first element. The arrangement of the two elements, together with their openings, with respect to one another thereby forms individual chambers, specifically for an opening of the second element, since that opening, on the one hand, is closed off on its second side, and, on the other hand, the layer is arranged on the first side of the second element. The first element, the layer, and the second element can be arranged directly against one another or mounted on one another, so that no further components or interstices are provided therebetween. It would also be conceivable, however, to provide between the layer and the second element components, for example a sealing ring, that could be arranged in an external region of the apparatus according to the present invention. An opening of the first element could, if necessary, likewise be closed off from the external environment with the aid of a covering.

What has been recognized according to the present invention is firstly that a region constituted by an opening is provided in one of the elements in the apparatus. The biological specimen to be processed by laser microdissection is introduced into this region. This region or opening is physically isolated, by the layer, with respect to the alignedly arranged opening of the other element. It can also be physically isolated from the environment. By means of a laser microdissection operation, a portion of the biological specimen can be conveyed, by way of the layer, from the opening in which that biological specimen is located into the other opening, in which context that portion of the biological specimen does not come into contact with the external environment. The biological specimen, as well as the portion of a biological specimen cut out by means of a laser microdissection operation, correspondingly remains inside the apparatus according to the present invention throughout the relevant processing thereof, so that in advantageous fashion, no contamination from the environment can occur. A fall over a long distance from the modified Petri dish into a collection container as in DE 102 34 755 A1, or an upward catapulting as in WO 2006/024392 A2, in which the microdissected portion of the biological specimen necessarily comes into contact with the external environment, are prevented by the apparatus according to the present invention.

The at least one biological specimen is arrangeable in a region of the layer facing away from the second element. A portion of the biological specimen is then conveyable by way of a laser microdissection operation into an opening of the second element. In other words, the biological specimen is located in an opening of the first element. The biological specimen could, for example, be arranged directly on the layer. A liquid or a nutrient medium with which in vivo conditions could be constituted for the biological specimen could, however, additionally be provided in the opening.

There are two fundamentally different methods for separating a portion of the biological specimen. These are on the one hand falling in response to gravity, as described by way of example in DE 102 34 755 A1, and on the other hand the upward catapulting described by way of example in WO 2006/024392 A2.

Accordingly, in a first embodiment the apparatus according to the present invention is embodied, and is introducible into a laser microdissection device, in such a way that the second element is arranged below the first element. Conveyance of the microdissected portion of the biological specimen from the region of the layer facing away from the second element into an opening of the second element is achievable by gravity after the portion has been freed by a cutting line.

According to a second embodiment, the apparatus according to the present invention is embodied, and is introducible into a laser microdissection device, in such a way that the first element is arranged below the second element. Conveyance of the microdissected portion of the biological specimen from the region of the layer facing away from the second element into an opening of the second element (i.e. upward) is achievable in this case by laser pressure catapulting (LPC).

In another embodiment, a covering is provided which is attachable to the apparatus in such a way that the openings of the first element are covered with respect to the environment. Such a covering could be configured so that each opening of the first element is individually covered. It would thereby be possible, for example, to create for biological specimens in the one opening internal environmental conditions that are different as compared with biological specimens in other openings. Alternatively, the covering could also be configured in such a way that all the openings of the first element are covered together, by which means, for example, the same internal environmental conditions for the biological specimens arranged in the openings could be created in relatively simple fashion. Attachment of the covering could be embodied reversibly, so that removal of the covering is possible in order, for example, to introduce nutrient medium or the like at a later time. In this context the covering could be embodied, and could coact with the first element, in such a way that a sterile covering of the openings of the first element is achievable, i.e. so that both liquid exchange and gas exchange with the environment is largely preventable.

The first element could be configured in the form of a rectangular or round plate, having sides arranged parallel to one another, having a definable thickness, for example 3 to 8 mm. The at least one opening that extends from the first side of the element to the second side of the element could be of rectangular or rounded, or round, configuration. The diameter of a round opening of the first element could be approximately 5 mm.

The second element could also be embodied in the form of a rectangular or round plate, having sides arranged parallel to one another, having a definable thickness. The at least one opening that extends from the first side of the element into the second element could be rectangular or round in configuration. A round opening of the second element could have a diameter of approximately 5 mm. If the first element is rectangular in shape, it is useful also to embody the second element in rectangular form, preferably in such a way that the two elements are substantially congruent when mounted on one another. The same applies to a substantially round embodiment of the two elements.

The region closing off the opening of the second element with respect to a second side, located opposite the first side, of the second element could be embodied in the form of a base. This base could comprise a glass plate or could be embodied in one piece with the second element. The thickness of the base could be less than 0.5 mm. If the apparatus according to the present invention is embodied, and is introducible into a laser microdissection device, in such a way that the first element is arranged below the second element, the term "lid" rather than "base" would instead be used.

The second element could be embodied in the form of a multititration plate or in the form of a multi-well plate or in the form of a microslide having eighteen openings, in which context the second element could be a microslide obtainable under the designation "µ-slide 18-well flat" from the company styled iBiDi, Integrated BioDiagnostics, Schellingstrasse 4, 80799 Munich. Because such components are obtainable commercially and occasionally also at a low price, the apparatus according to the present invention can be represented as having an economically low cost.

In a further embodiment, the layer closing off the opening of the second element with respect to a second side, located opposite the first side, of the second element could be embodied in the form of a film attached to the second side of the second element. The second element could to that extent be embodied to be substantially identical in design to the first element. As a result, for example, a microdissected portion that had been conveyed by means of a laser microdissection operation from an opening of the first element into the opening, aligned therewith, of the second element could be subjected again to a further laser microdissection operation so that further processing, and if applicable further separation, of the biological specimen or a portion thereof is advantageously possible. For this purpose, a further element, substantially identical in design to the second element of this embodiment, could be adapted from the second side of the second element, specifically in such a way that the at least one opening of the second element aligns with at least one opening of the further element.

The layer and/or the closing-off region of the second element preferably comprises a polymer film, which can be a laser-light-absorbing film. This film could comprise, for example, polyethylene naphthalate (PEN) or polyethylene terephthalate (PET) or polyethylene (POL). The specific type of film selected will depend substantially on the respective biological or medical application. The film could be welded or adhesively bonded to the first and/or second element. Care must be taken here that the mounting of the film to the first or second element is embodied in such a way that, depending on the particular application, on the one hand sterility is maintained and on the other hand survival of the biological specimens is possible. The mounting should therefore, as a rule, not be detachable by the liquids or nutrient solutions used.

Because the laser microdissection operation is, as a rule, optically monitored or controlled with the aid of a microscope, it is useful for the first element, the second element, and/or the covering to comprise an optically transparent material, for example glass or plastic, in particular polycarbonate. The dimensions of the apparatus according to the present invention, in particular in the direction of the optical axis or in the longitudinal direction of the openings, may furthermore be such that the biological specimen or the layer is focusable and thus observable using a suitable microscope objective. This applies in the same fashion, in particular, to the focusing of the laser light provided for the laser microdissection operation. Microscope objectives having a relatively long working distance could accordingly be used.

If the biological specimen is equipped with fluorescent markers or if fluorescence applications in general are being carried out, it is advantageous if the first element, the second element, and/or the covering comprise or comprises no autofluorescent material. There are accordingly no, or almost no, interfering fluorescent light contributions that proceed from the apparatus according to the present invention.

In an embodiment, the adaptation of the first element onto the second element is embodied reversibly. This could be achieved, for example, with the aid of snap-lock means or fastening means. In particular, the adaptation of the first element onto the second element, and if applicable onto the layer, could be embodied sealingly, so that a closure with respect to the environment is produced at least by way of this join; this can largely prevent contamination.

If a further laser microdissection is to be carried out on a microdissected specimen portion that has been conveyed out of an opening of the first element, as a result of a first laser microdissection operation, into an opening of the second element, for example in order to separate a further portion from the microdissected specimen portion, provision can be made in an embodiment for at least one further element, substantially identical in design to the second element or to the second element, to be attachable to the second element from the side of the second element facing away from the first element. The layer embodied, for example, in the form of a film is accordingly provided between the first element and the second element. A further layer that is embodied, for example, in the form of a film is provided between the second element and the further element. On the side of the further element facing away from the further layer, the further element can comprise a base-like closure or likewise a layer or a film. The apparatus according to the present invention, together with the respectively provided layers, could accordingly be introduced into a laser microdissection device already fitted with three elements. It is also conceivable, however, for the apparatus according to the present invention, initially comprising two elements and the layer, to be taken out of the laser microdissection device after a first laser microdissection operation, and for a further element to be attached to the second element. The covering could be attached to the second element in order to cover it. Attachment of the further element could be accomplished reversibly, for example using snap-lock or fastening means, or using an adhesive film. Attachment of the further element could once again usefully be performed sealingly with respect to the external environment, in order largely to prevent contamination of the specimen portion.

Depending on the particular application, provision can be made for a cell culture medium, a nutrient medium, and/or a liquid to be provided in at least one opening of the first and/or of the second element. This action can promote longer survival of the biological specimens, but can also be expedient as a preparation for subsequent further processing steps.

Specifically because the apparatus according to the present invention is suitable for laser microdissection of living biological specimens, according to an embodiment at least one means can be provided with which, for a living biological specimen present in the apparatus, an environmental condition necessary for survival of the specimen is producible. This means could also be associated with the apparatus according to the present invention, for example in the form of a container which is adaptable to the apparatus according to the present invention and/or into which the apparatus according to the present invention is introducible. A means of this kind could comprise, for example, a heating means with which the apparatus, and the biological specimens present therein, can be kept at a definable temperature. A temperature of this kind can be, for example, 36 degrees Celsius. Alternatively or additionally, a means can be provided with which a definable atmospheric composition that surrounds the biological specimen is achievable and can be held substantially constant. An atmospheric composition of this kind could be, for example, a definably settable mixing ratio of oxygen and nitrogen. Hose connections between a supply tank and the apparatus according to the present invention could correspondingly be provided for this purpose.

An apparatus according to the present invention may be used in a laser microdissection device for laser microdissection of at least one (preferably living) biological specimen, the at least one biological specimen being arrangeable in the apparatus in such a way that it remains in the apparatus as a result of a laser microdissection operation. In principle, the apparatus according to the present invention can be used for very different applications or method steps, for example for a PCR. The apparatus according to the present invention is advantageously suitable, for laser microdissection on biological specimens present in the apparatus. In advantageous fashion, the apparatus according to the present invention can be used for a laser microdissection device that is adapted onto an upright microscope. In an embodiment, the apparatus is embodied, and is used in the laser microdissection device, in such a way that the second element of the apparatus is arranged below the first element; and that a portion of the biological specimen arranged in an opening of the first element is conveyed by gravity, as a result of the laser microdissection operation on the layer, into an opening of the second element.

Be it also noted that in principle, depending on the size of the cut-out sample regions, a nutrient liquid surrounding the biological specimen cannot, because of surface tension, pass through the usually microscopically small holes that have been created in the laser-cuttable film during laser microdissection. If larger holes are produced, the nutrient liquid may possibly flow out therethrough and, in some circumstances, be lost. It therefore proves to be advantageous if the surrounding medium of the biological specimen, or the nutrient medium, is embodied as a nutrient gel which is sufficiently solid, or at least viscous enough, that it "stays put" around the holes produced by microdissection in the laser-cuttable film.

The apparatus according to according to the present invention plays an important role in the method according to the present invention, so that in order to avoid repetition, the reader is referred at least in that regard to the foregoing portion of the description, the properties and advantages of the method being revealed to one skilled in the present art having a knowledge of what is disclosed by the foregoing portion of the description.

In order to control the laser and the microdissection operation, the laser microdissection device could comprise a control device. The control device can be embodied in the form of a computer or personal computer that comprises, for example, a monitor on which is displayed an image of the biological specimen to be processed. The control device could serve to program the microdissection operation and could determine the cut line by means of digital image processing methods. What is meant by "programming" in this connection is, in particular, definition of the specimen portion that is to be cut out. This could, for example, be achieved by image processing. Alternatively or additionally, in order to program the control device an operator could interactively encircle the specimen region of interest, for which purpose he or she can use an input unit of the control device (e.g. a mouse, joystick, graphics tablet) in combination with an output unit of the control device (e.g. a monitor for displaying the specimen).

A definition of the planned cut line using the digital image processing methods could be performed, for example, in accordance with a user's inputs, in which context the user defines a characterizing specimen peculiarity (e.g. a specific abnormal cell shape), after which a suitable image processing routine carries out an automatic specimen segmentation. The result of the specimen segmentation could optionally be displayed to the user for monitoring or confirmation.

Depending on the particular task or application, the specimens that have been selected and conveyed into the opening of the second element could be further processed using biological or chemoanalytical further processing or evaluation methods. Examples of such further processing or evaluation methods are the polymerase chain reaction (PCR) or a digestion reaction.

The fact that the first element is preferably reversibly mountable onto the second element advantageously makes it possible to perform the further processing or evaluation methods on the at least one specimen portion in the second element. Specifically, the first element can be removed from the second element for that purpose. Only the second element having the specimen portion to be further processed can therefore serve for further processing. Depending on the further processing steps, it might be useful to cover the second element with a covering in order to protect the specimen portion, present in the second element, from contamination by the external environment. But a subsequent further processing of the specimen portion in the second element is likewise conceivable even if the first element is not removed from the second element.

The further processing or evaluation method could encompass, in particular, another laser microdissection operation using a laser microdissection device. A further element substantially identical in design to the second element or to the second element could accordingly be attached to the second element from the side of the second element facing away from the first element, so that after another laser microdissection operation, a portion of the biological specimen present in an opening of the second element is conveyed into an opening of the further element.

FIG. 1 shows a laser microdissection device 1 in which a first exemplifying embodiment of an apparatus 2 according to the present invention for receiving biological specimens is introduced. With laser microdissection device 1, a laser beam is moved, during cutting, over the biological specimen that is arranged in stationary fashion relative thereto. Laser microdissection device 1 encompasses a microscope 3 having a microscope stand 4 and an X-Y stage 5 movable in motorized fashion. X-Y stage 5 serves to receive apparatus 2 and to position apparatus 2 relative to microscope 3.

To allow the biological specimen in apparatus 2 to be illuminated from below, X-Y stage 5 comprises a frame-shaped stage opening 6. Microscope 3 is a transmitted-light microscope. An illumination system 7 and a condenser 8, with which the biological specimen in apparatus 2 can be illuminated, are arranged for that purpose under X-Y stage 5 and thus also below the biological specimen in apparatus 2. The light penetrating through the specimen travels to objective 9 of microscope 3. Within microscope 3, the light is conveyed via lenses and mirrors (not shown in FIG. 1) to at least one eyepiece 10 through which an operator can view the specimen arranged on X-Y stage 5.

A laser beam 12 proceeds from a laser 11 (in this exemplifying embodiment a UV laser) and is coupled into an incident illumination beam path having an optical axis 13. A laser scanning device 14 is arranged in the illumination beam path. Laser beam 12 passes through laser scanning device 14 and travels via an optical system 15 to objective 9, which focuses laser beam 12 onto the biological specimen in apparatus 2. Optical system 15 is preferably embodied as a dichroic beam splitter through which an imaging beam path, proceeding from the biological specimen through objective 9, travels to at least one eyepiece 10. Alternatively, optical system 15 can be made up of multiple optical components. This is the case, for example, when laser beam 12 must be deflected several times.

Also provided in laser beam 12 is a stop 16 with which the diameter, and thereby the aperture, of laser beam 12 is adjustable. Stop 16 can be embodied, for example, as a fixed stop. In an advantageous embodiment, multiple fixed stops can be arranged on a rotating disc or on a linear slider in order to introduce one of these fixed stops into the beam path as the respectively required stop 16. Introduction into laser beam 12 can be carried out manually by the user, or in motorized fashion.

In this embodiment, the adjustment of laser scanning device 14, and thus the displacement of laser beam 12 onto the biological specimen, is accomplished using a motor 17 associated with laser scanning device 14, a control unit 18, and a control computer 19. Motor 17 is connected to control unit 18, which supplies the control signals for controlling motor 17. Control unit 18 is connected to computer 19, to which a monitor 20 is connected. The image of the biological specimen acquired by a camera 21 is displayed on monitor 20. The system made up of control computer 19, camera 21, and monitor 20 serves for observation and monitoring of the cutting operation. For example, control computer 19 can deliver to laser 11 triggering signals to initiate laser pulses and to control laser power output, to control stop motor 22, and to control an autofocus device for laser 11. For that purpose, control computer 19 is connected to laser 11 via a control line, and furnishes the latter with triggering signals to initiate laser pulses when a cutting operation is to be carried out.

By means of a computer mouse or any other cursor control device, the sample region of interest that is to be cut out of the biological specimen is outlined on monitor 20. In this fashion, a desired target cutting line in defined on monitor 20 in the camera image.

Laser scanning device 14 itself serves as a cut-line control unit that, during the cutting operation, moves laser beam 12, which is focused onto the biological specimen, over the biological specimen that is arranged in stationary fashion. During the cutting operation, X-Y stage 5 is accordingly not displaced horizontally, i.e. in the X direction and Y direction. A displacement of X-Y stage in the context of a laser beam arranged in stationary fashion is of course also conceivable for laser microdissection.

Focusing of laser beam 11 onto the biological specimen can be accomplished by manual vertical adjustment at focus knob 23 of X-Y stage 5 with simultaneous visual monitoring of the camera image by a user. An embodiment of the apparatus that encompasses an autofocus apparatus for laser beam 11 is, however, more user-friendly.

Laser beam 11 can be guided to any desired positions on the biological specimen by control of laser scanning device 14, provided the specimen is located in the object field of objective 9. The biological specimen can be kept alive throughout the preparation for cutting and even during cutting itself, since growth conditions are constantly maintained in apparatus 2.

By suitable control exerted on laser scanning device 14, the focused laser beam 11 is moved over the biological specimen and a continuous cut line is thereby generated around the selected specimen region or the specimen region of interest. The specimen region of interest itself is at no time irradiated by the laser radiation, so that any damaging effect of laser radiation on the specimen region of interest is precluded. Once the cut line is complete, the specimen region of interest is completely detached from the remainder of the specimen surrounding it, and falls in response to gravity into an opening of the second element arranged under the first element of apparatus 2 thereunder.

FIG. 1 accordingly shows the use of an apparatus 2 in a laser microdissection device 1 for laser microdissection of at least one biological specimen, the at least one biological specimen being arrangeable in apparatus 2 in such a way that it remains in apparatus 2 as a result of a laser microdissection operation. The configurations of the individual exemplifying embodiments of apparatus 2 according to the present invention will be discussed in more detail below with reference to FIGS. 2 to 11.

Figure 2:
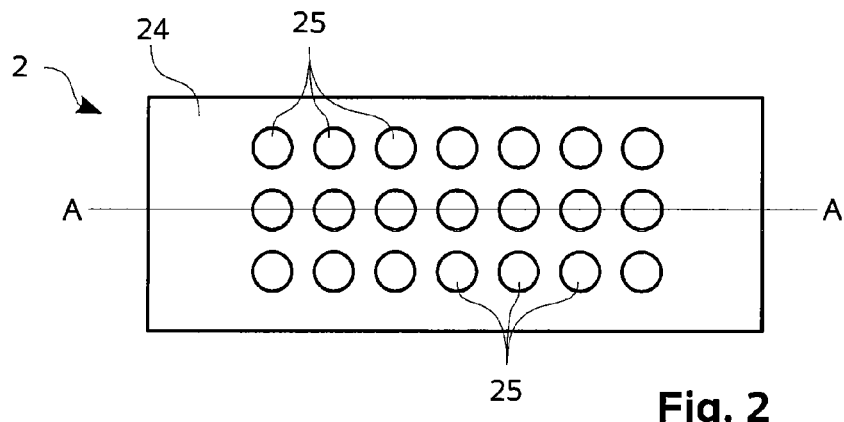
FIG. 2 is a plan view of an exemplifying embodiment of an apparatus according to the present invention for receiving biological specimens.

FIG. 2 schematically depicts a plan view of an exemplifying embodiment of an apparatus 2 according to the present invention for receiving biological specimens. Apparatuses 2, or portions thereof, that are shown in sectioned view in FIGS. 3 to 11 are depicted in comparable fashion in the plan view.

FIG. 2 shows the exemplifying embodiment of apparatus 2 according to the present invention from above. First element 24 of apparatus 2 is accordingly visible. First element 24 comprises multiple openings 25 of circular cross section into which biological specimens can be introduced. In the exemplifying embodiment according to FIG. 2, a total of twenty-one openings 25 are provided. It is likewise conceivable to use an apparatus that comprises eighteen openings; the eighteen openings could be arranged in three columns and six rows, as is the case, for example, in a "μ-slide 18-well flat" of the iBiDi company. In the latter slide, both the first and the second element 24, 29 each have eighteen openings 25, 30, which have a diameter of approx. 5 millimeters and into which a liquid volume of approx. 30 μl can be introduced. Only a small quantity of cell culture medium or nutrient medium is accordingly necessary, so that it is possible to work economically.

Figure 3:
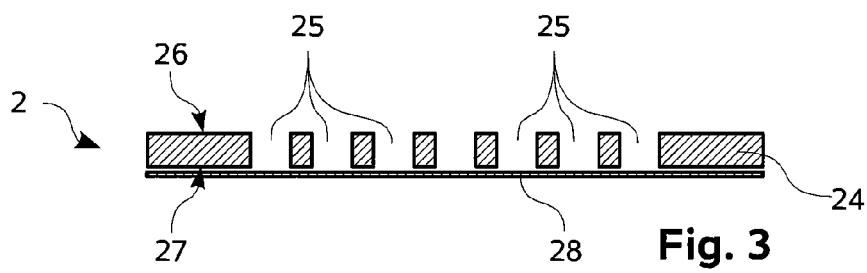
FIG. 3 is a sectioned view of the first element and of the layer, along line A-A of FIG. 2.

FIG. 3 shows first element 24 in a sectioned view along line A-A of FIG. 2. It is correspondingly apparent that openings 25 of first element 24 extend from first side 26 of first element 24 to second side 27 of first element 24. First side 26 of element 24 is arranged substantially parallel to second side 27 of first element 24. Layer 28 is attached to second side 27 of first element 24; for greater clarity of depiction, a small interstice is shown between first element 24 and layer 28 but is not in fact present when apparatus 2 is in the completely assembled state. Layer 28 is embodied in the form of a polyethylene naphthalate (PEN) film, and is adhesively bonded onto second side 27 of first element 24, specifically in such a way that liquids or nutrient solutions that can be introduced into openings 25 remain in them. In other words, layer 28 closes off openings 25 at the bottom in sealing fashion (in particular for liquids, but also for gases).

Figure 4:
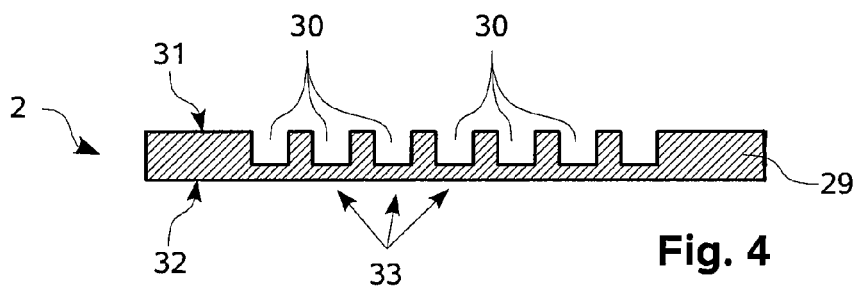
FIG. 4 is a sectioned view of the second element, along line A-A of FIG. 2.

FIG. 4 shows second element 29, once again in a sectioned depiction along line A-A of FIG. 2. Second element 29 comprises openings 30 that extend from first side 31 of second element 29 into second element 29. Openings 30 are closed off with respect to second side 32, located opposite first side 31, of second element 29. A respective base 33 having a thickness of less than 0.5 mm is accordingly provided there (identified by arrows).

Second element 29 is embodied on one piece. It could be manufactured using an injection-molding shaping method. It would also be conceivable to equip a corresponding plate with blind holes, which then form openings 30.

Figure 5:
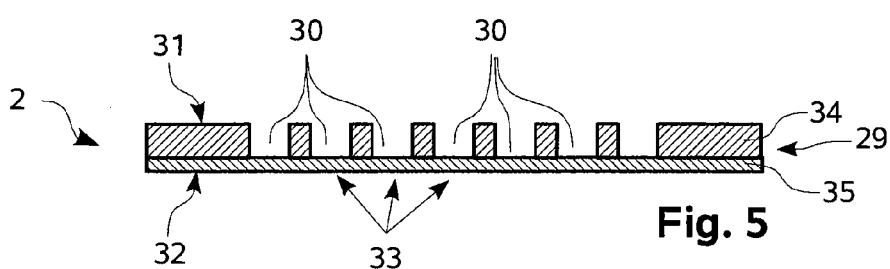
FIG. 5 is an exemplifying embodiment of a second element as an alternative to FIG. 4.

FIG. 5 shows an alternative embodiment of second element 29, likewise in a sectioned depiction. Here a plate 34 equipped with holes is provided, which plate could be substantially identical in design to first element 24 of FIG. 3. A glass plate 35 is attached to plate 34 from the lower side of the plate, so that in a manner comparable to FIG. 4, openings 30 are once again formed that extend inward from first side 31 of second element 29. Second element 29 according to this exemplifying embodiment is correspondingly embodied in two parts.

Figure 6:
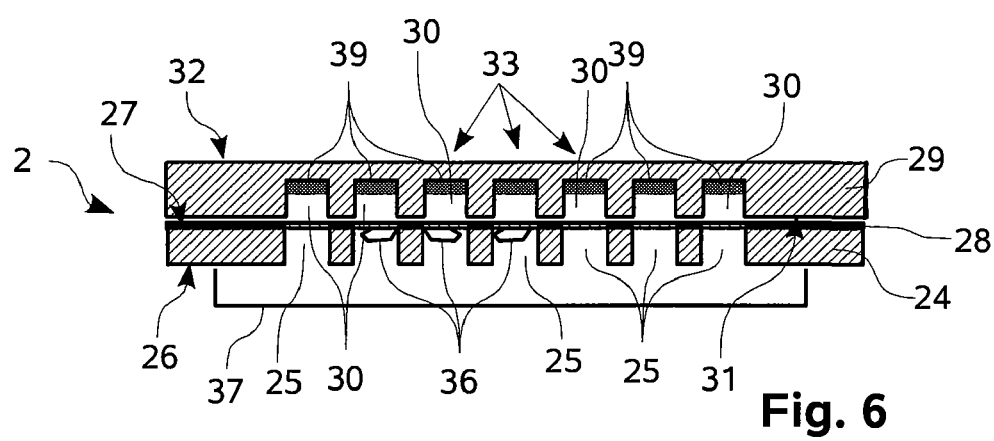
FIG. 6 shows an exemplifying embodiment according to the present invention of an apparatus having biological specimens, prior to laser microdissection.
Figure 7:
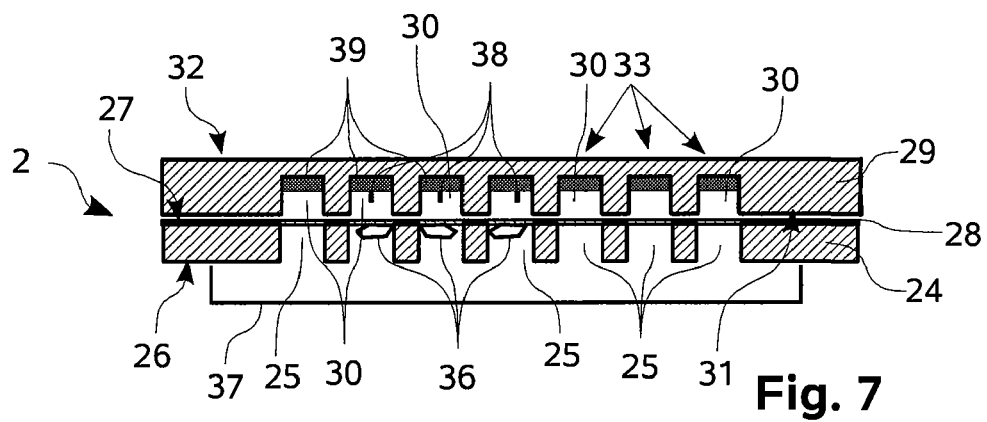
FIG. 7 shows the exemplifying embodiment according to FIG. 6 after laser microdissection has been performed.

FIGS. 6 and 7 show, in a sectioned depiction, an exemplifying embodiment of an apparatus 2 according to the present invention that comprises first element 24, layer 28, and second element 29. These components are put together in such a way that second side 27 of first element 24 is arranged adjacent to first side 31 of second element 29. Layer 28 is arranged between second side 27 of first element 24 and first side 31 of second element 29. Layer 28 on the one hand seals off openings 25 of first element 24 with respect to second element 29. On the other hand, layer 28 seals off openings 30 of second element 29 with respect to first element 24. Merely for clarity of depiction, a small interstice is provided between first side 31 of the second element and layer 28, but in an actually assembled apparatus 2 it is not present or is filled with corresponding adhesive. First element 24 is oriented with respect to second element 29 in such a way that openings 25 of first element 24 align with openings 30 of second element 29. A respective biological specimen 36 is introduced into three of the openings 25 and adheres respectively to layer 28. Openings 25 of first element 24 are covered with respect to the external environment by a covering 37.

Apparatus 2 of FIG. 6, in the state shown therein, is introduced into a laser microdissection device having an inverted microscope (not shown). After a respective specimen portion of interest has been cut out of each of the three specimens 36 and conveyed by LPC upward into the respective openings 30, the three specimen portions 38 are arranged in an upper region of openings 30 (see FIG. 7). Specimen portions 38 adhere to nutrient medium 39 arranged at the upper end of openings 30.

Figure 8:
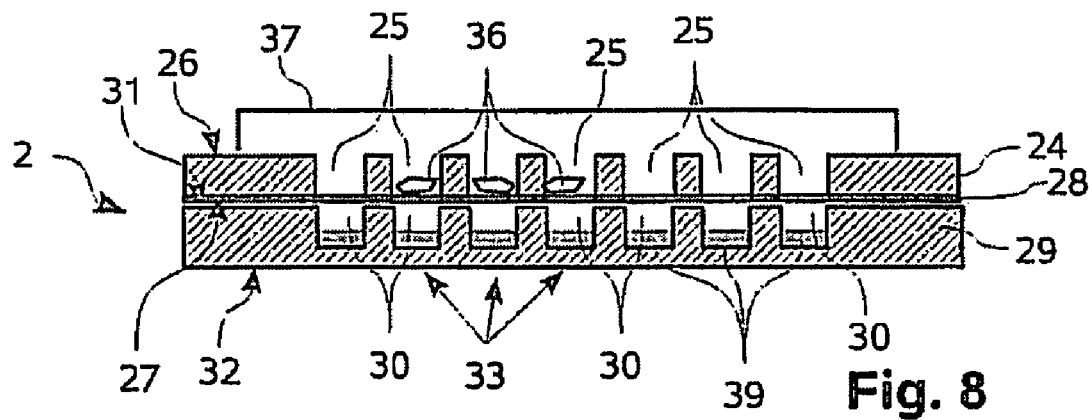
FIG. 8 shows a further exemplifying embodiment according to the present invention of an apparatus having biological specimens, prior to laser microdissection.
Figure 9:
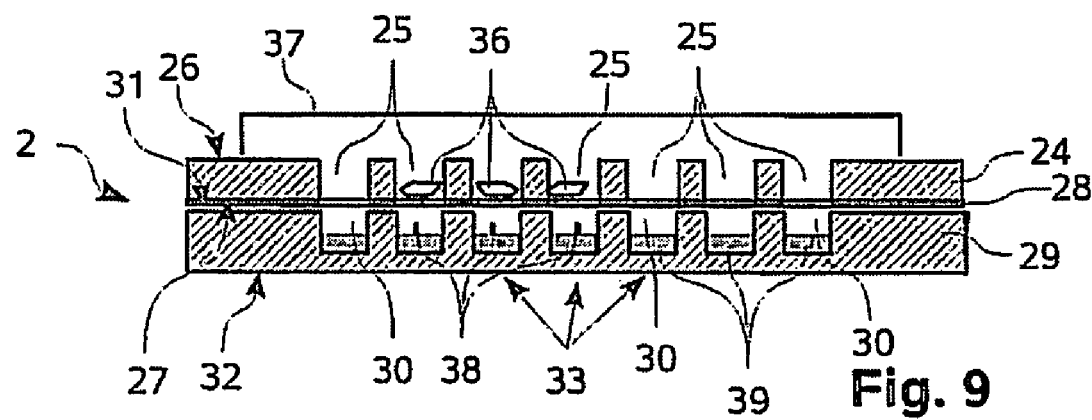
FIG. 9 shows the exemplifying embodiment according to FIG. 8 after laser microdissection has been performed.

FIGS. 8 and 9 show an apparatus 2, substantially comparable to FIGS. 6 and 7, for receiving biological specimens. Here apparatus 2 is introduced, in the state shown therein, into a laser microdissection device having an upright microscope (not shown). Three specimens 36 are also arranged in apparatus 2 according to FIG. 8, and a specimen portion of interest is cut out of each of them. Second element 29 is arranged below first element 24, specifically in such a way that second side 27 of first element 24 is arranged adjacent to first side 31 of second element 29. An optically transparent covering 37 arranged on first element 24 isolates openings 25 from the external environment. In apparatus 2 according to the exemplifying embodiment of FIGS. 8 and 9, the specimen region of interest, and layer 28 arranged thereunder and embodied in the form of a film, are cut out by means of a continuous cut line. Both the specimen region of interest and the film piece arranged thereunder respectively fall, in response to gravity, into openings 30 of second element 29, where they can be conveyed on base 33, in nutrient medium 39, for further processing.

Figure 10A:
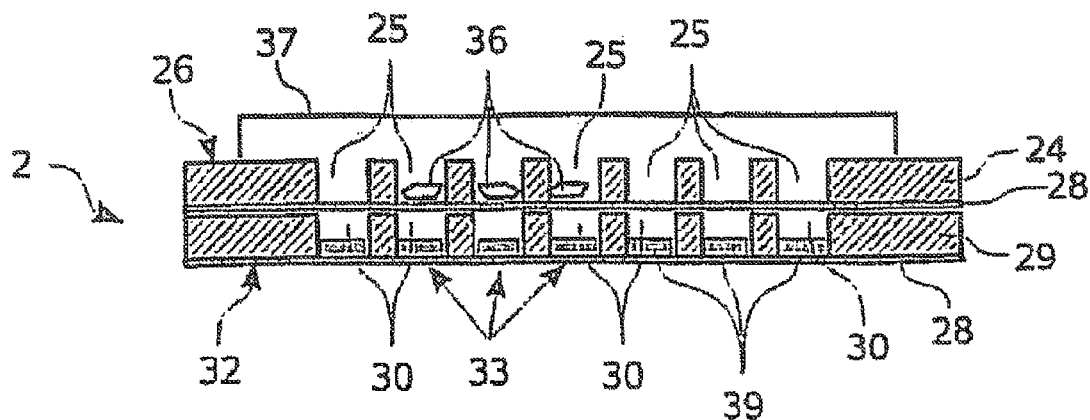
FIG. 10A shows a further exemplifying embodiment according to the present invention of an apparatus having biological specimens, prior to laser microdissection.
Figure 11:
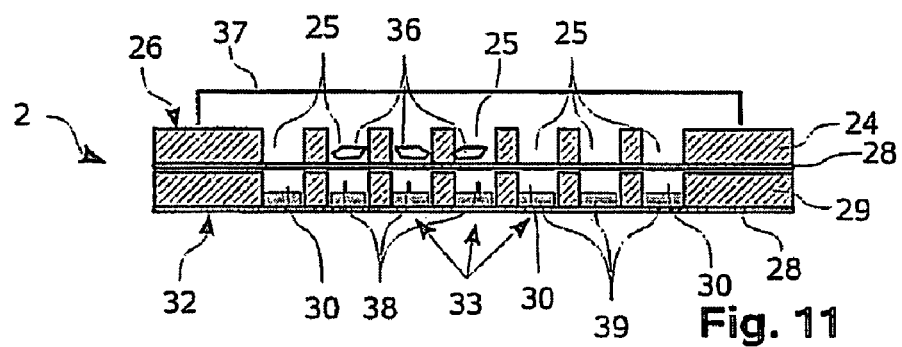
FIGS. 11 and 12 show the exemplifying embodiment according to FIGS. 10 and 11, respectively, after laser microdissection has been performed.

FIGS. 10A and 11 show, once again in a sectioned depiction, a further exemplifying embodiment of apparatus 2 that is introduced, in the state shown therein, into a laser microdissection device of an upright microscope (not shown). Both covering 37 and first element 24, and layer 28 arranged thereunder, are embodied comparably to the exemplifying embodiment of FIGS. 8 and 9. Second element 29 of FIGS. 10A and 11 is embodied comparably to first element 24 of FIGS. 10A and 11. Accordingly, a further layer 28 that is likewise embodied in the form of a film is arranged below second element 24. Accordingly, layer 28 for closing off openings 30 of second element 29, which layer is arranged below the plate-shaped component of second element 29, forms a base-like region 33. Biological specimens 36, from which specimen regions of interest 38 are respectively cut out by means of laser microdissection, are also arranged in apparatuses 2 according to FIGS. 10A and 11. The operation for cutting specimen regions of interest 38 out of biological specimens 36 according to FIG. 10A and conveying them into second element 29 (as shown in FIG. 11) is substantially comparable to the operation that was described with reference to FIGS. 8 and 9.

Figure 10B:
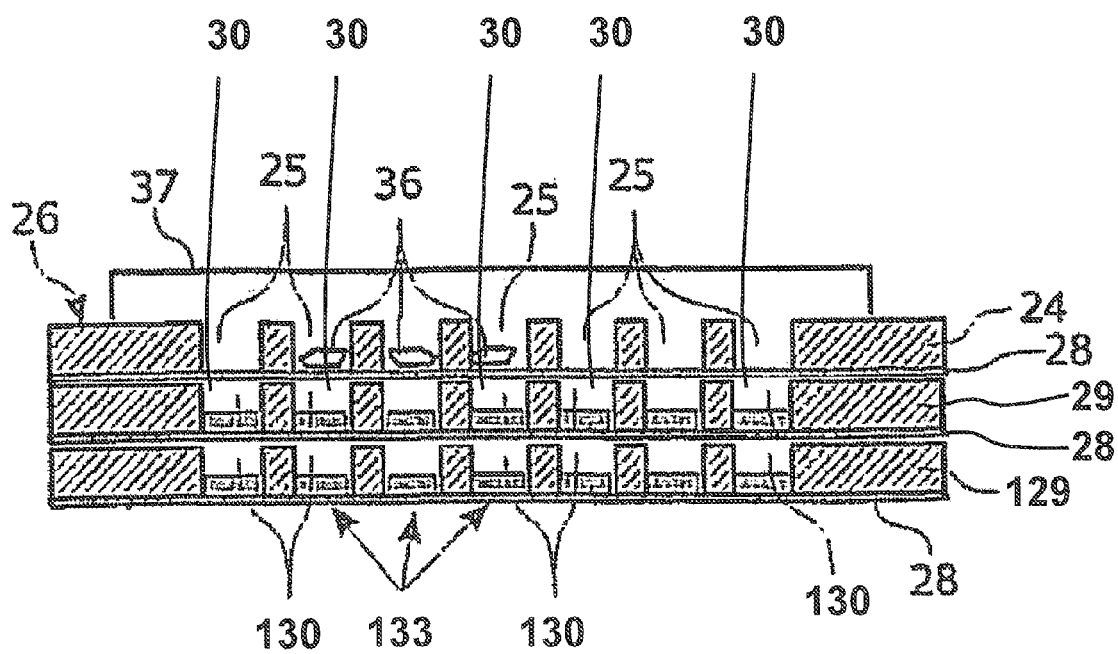
FIG. 10B shows a further exemplifying embodiment according to the present invention of an apparatus having a further element and biological specimens, prior to laser microdissection.

FIG. 10B shows a sectioned depiction of a further exemplifying embodiment similar to the embodiment of FIG. 10A, but having included a further element 129 that facilitates a further laser microdissection to be carried out on a microdissected specimen portion that has been conveyed out of an opening 25 of the first element 24, as a result of a first laser microdissection operation, into an opening 30 of the second element 29, for example in order to separate a further portion from the microdissected specimen portion. Further element 129 is embodied comparably to second element 29. A layer 28 embodied, for example, in the form of a film is accordingly provided between the second element 29 and the further element 129. A further layer 28 that is likewise embodied in the form of a film is arranged below further element 129. Accordingly, layer 28 below further element 129 for closing off openings 130 of further element 129, forms a base-like region 133.

Specimens 38 that have been selected and conveyed into opening 30 of second element 29 can then be further processed using biological or chemoanalytical further processing or evaluation methods. Examples thereof are polymerase chain reaction (PCR) methods or biological digestion reactions. The further processing or evaluation methods for the at least one specimen portion 38 are performed directly in second element 29, which can optionally be covered with a covering. For that purpose, first element 24 is removed from second element 29.

Figure 12:
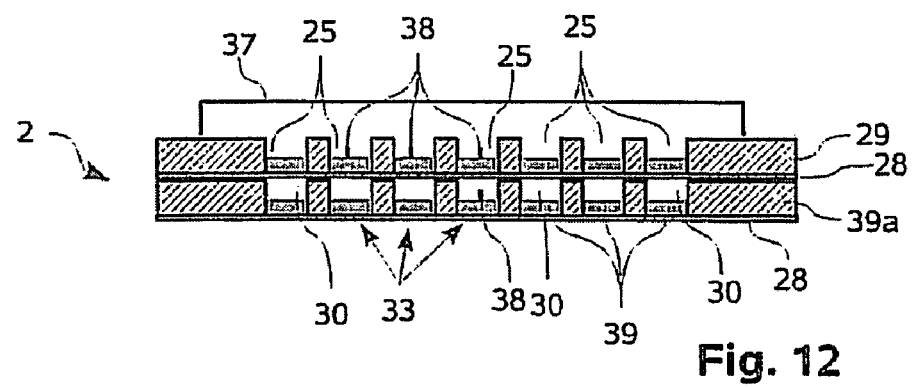

The further processing or evaluation method could encompass another laser microdissection using a laser microdissection device 1 according to FIG. 1, apparatus 2 provided for that purpose being shown in FIG. 12. Second element 29 is covered with a further covering 37. A further element 39a that is embodied comparably to second element 29 of the same Figure is then attached below second element 29. FIG. 12 shows an apparatus 2 in which a further specimen region of interest 38 of one of the three cut-out specimen regions 38 has been conveyed by means of laser microdissection into further element 39a in the fourth opening 30 from the left.

First element 24, second element 29, and/or covering 37 comprise an optically transparent material that may be made, for example, of plastic, specifically polycarbonate.

The adaptation of first element 24 onto second element 29 is accomplished reversibly. Correspondingly, first element 24 having layer 28 mounted thereon can be detached from second element 29. It is also conceivable for only first element 24 to be detached from second element 29, and for layer 28 to remain on the second element.

Figure 13:
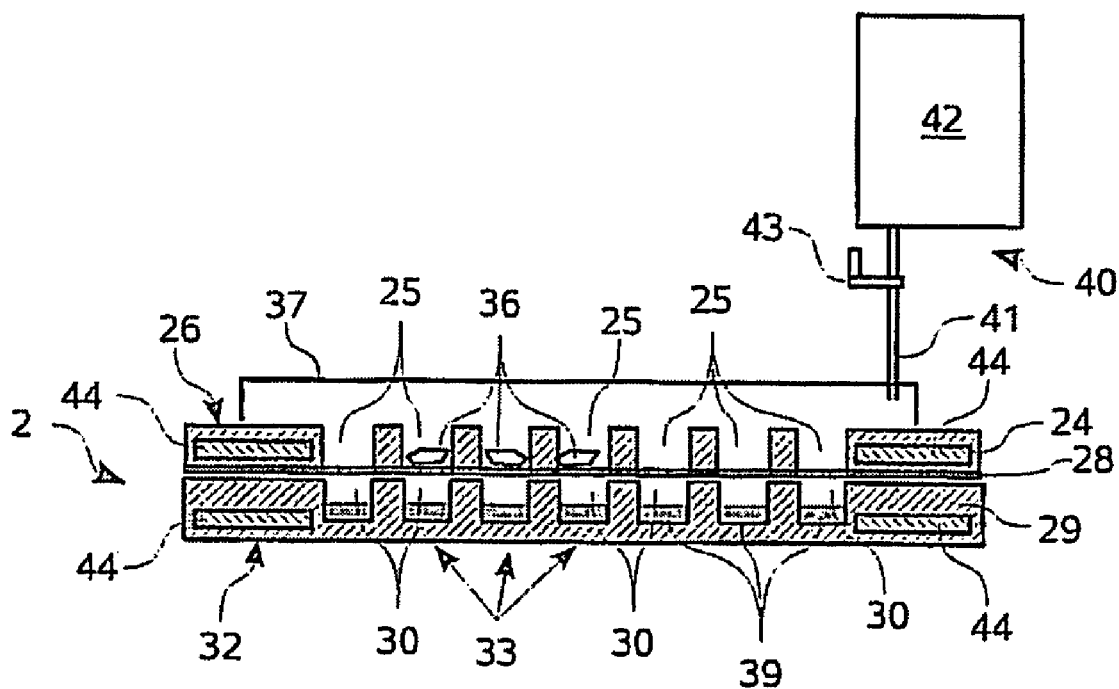
FIG. 13 is a sectioned depiction of an apparatus according to the present invention, comparable to FIG. 8, having a means with which a desired environmental condition for biological specimens in the apparatus is achievable.
Figure 14:
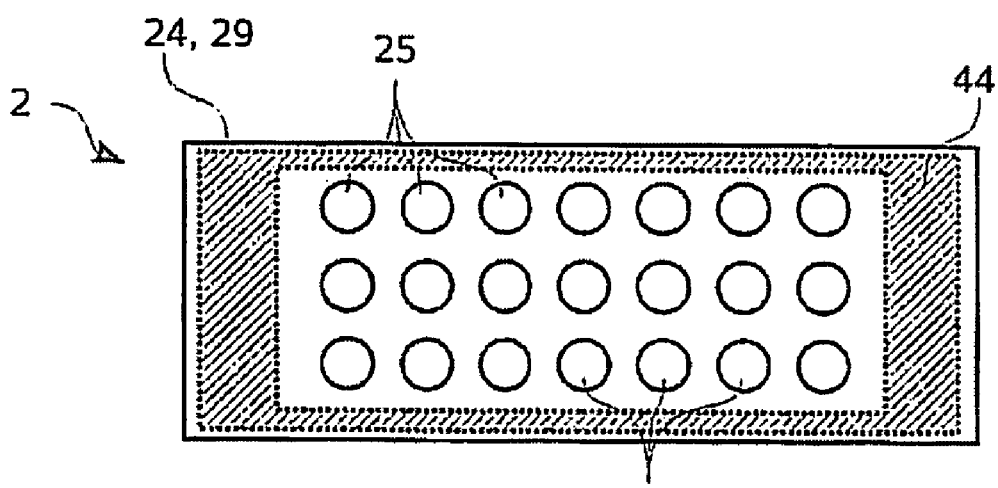
FIG. 14 is a plan view of the exemplifying embodiment according to FIG. 13.

FIG. 13 indicates, merely schematically, that a means 40 for making available suitable environmental conditions for the living biological specimens 36 present in apparatus 2 is provided. Apparatus 2 according to FIG. 13 has a configuration comparable to apparatus 2 of FIG. 8. Means 40 encompasses a connecting line 41 that comprises a first end projecting into covering 37 and is connected to a gas source embodied in the form of a gas tank 42. A gas having a definable mixing ratio of oxygen and nitrogen is present in gas tank 42 and is conveyable at a suitable temperature into the region of apparatus 2 covered by covering 37. This is controllable with stopcock 43. Apparatus 2 shown in FIG. 13 furthermore comprises, both in first element 24 and in second element 29, a respective heating means 44 which is embodied in the form of a Peltier element and with which the internal region of apparatus 2 can be adjusted to a definable temperature (a temperature sensor and a regulating unit necessary for temperature regulation are not shown in FIG. 13). Heating means 44 is substantially frame-shaped and is arranged on the external region of apparatus 2 (see, for example, the shaded region in FIG. 14).

As already indicated, at least a principle of the underlying procedure in terms of a method according to the present invention for laser microdissection of at least one biological specimen is also apparent from FIGS. 6 to 14 and the descriptions provided for those Figures. According thereto, specimen 36 is firstly introduced into an apparatus 2 according to FIG. 6, 8, or 10, in a region of layer 28 facing away from second element 29. Apparatus 2 is covered with covering 37. Specimen 36 is introduced, with the respective apparatus 2, into a laser microdissection device. The apparatuses according to FIGS. 8 and 10 could be introduced, for example, in to a laser microdissection device 1 according to FIG. 1. A portion of specimen 36 is selected using laser microdissection device 1 or a microscope 3 adapted thereonto, a cut line being introduced into layer 28 around the selected specimen portion 38 by way of a cutting operation using a focusable laser light beam of laser microdissection device 1. The selected specimen portion 38 is conveyed into an opening 30 of second element 29.

Figure 15:
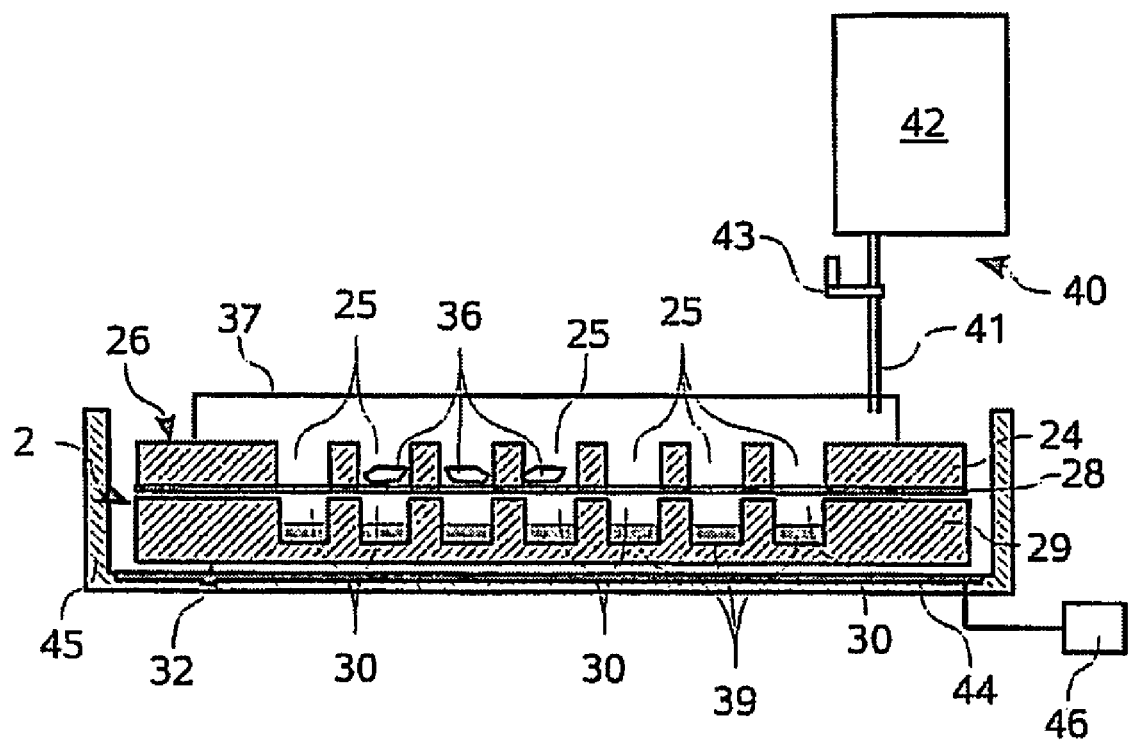
FIG. 15 is a sectioned depiction of an apparatus according to the present invention, comparable to FIG. 13, that is arranged in a container.

FIG. 15 shows, in a sectioned depiction, an apparatus 2 comparable to FIG. 13 but in which itself no heating element is integrated. Instead, in order to make available a desired or definable ambient temperature, a container 45 is provided in which a heating element 44 is integrated. Container 45 could substantially comprise a rectangular basal or base surface. A circular basal or base surface of container 45 would also be conceivable, in which context the container can then also be constituted in the form of a modified Petri dish. Heating element 44 comprises either a continuous rectangular basal surface or one comparable to FIG. 14. In the former case, transmitted illumination cannot be implemented. In the latter case, heating element 44 comprises a (rectangular or round) cutout through which light can pass for microscopic illumination or detection, and/or for laser microdissection. Heating element 44 is controlled by control unit 46 which, especially in the context of a Peltier element, encompasses a current source. Because heating element 44 is provided on container 45 and not directly in apparatus 2 according to the present invention, container 45 together with heating element 44 can advantageously be reused, whereas apparatus 2 according to the present invention can be discarded after a single use. Apparatus 2 according to the present invention can thus be offered more inexpensively, and can be made, by way of a standard holder and a container 45 having a heating element 45, into an in-vivo-capable apparatus. The entire apparatus 2 according to the present invention is thus introduced into container 45 shown in FIG. 15, in which context the container, with apparatus 2 according to the present invention, can be secured on microscope stage 5 of microscope 3. For efficient heat transfer, the underside of apparatus 2 according to the present invention is in immediate contact with the inner surface of container 45 and thus directly with heating element 44, a spacing between apparatus 2 and the container being depicted merely for the sake of clarity.

Figure 16:
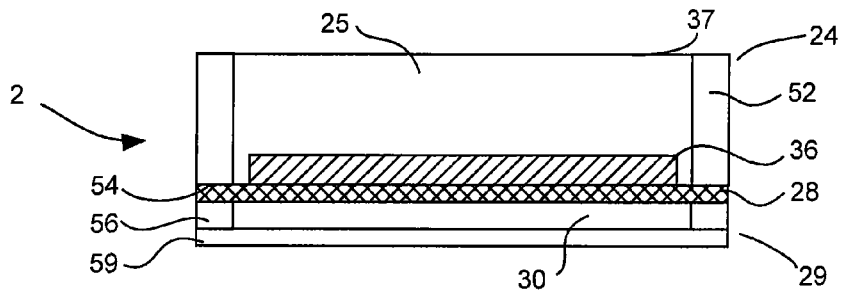
FIG. 16 is an exemplifying embodiment of an apparatus according to the present invention in the form of a petri dish having a film bottom extending over the entire bottom area.
Figure 17:
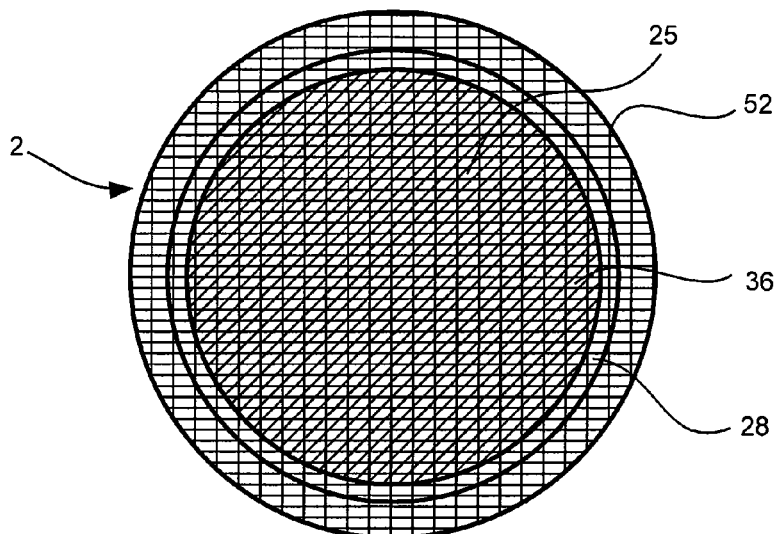
FIG. 17 is a plan view of the exemplifying embodiment according to FIG. 16, with the cover of the apparatus removed.

FIG. 16 is an exemplifying embodiment of an apparatus 2 according to the present invention in the form of a petri dish having a bottom formed by layer 28 extending over the entire bottom area. First element 24 is formed by a frame-like holder in the form of a cylindrical wall 52 of the petri dish, which is typically made of plastic. The petri dish has no plastic bottom. The missing plastic bottom of the petri dish is replaced by layer 28, in this case a laser light-absorbing and therefore laser-cuttable film, which is adhesively bonded to the bottom edge 54 of wall 52. The adhesive bond is resistant to a nutrient solution or a viscous nutrient gel to be applied later for the cell culture to be grown. Moreover, the adhesive is not cytotoxic in order to prevent damage to the biological preparation. Biological specimen is disposed on layer 28. Second element 29 is formed by cylindrical wall 56 and bottom 59. Opening 25 of first element 24 is aligned with opening 30 of second element 29 so that upon a cutting through of layer 28 in a laser microdissection operation a portion of biological specimen 36 falls into opening 30. Opening 25 may be covered with respect to the external environment by a covering 37. FIG. 17 is a plan view of the apparatus 2 according to FIG. 16 with cover 37 removed.

Figure 18:
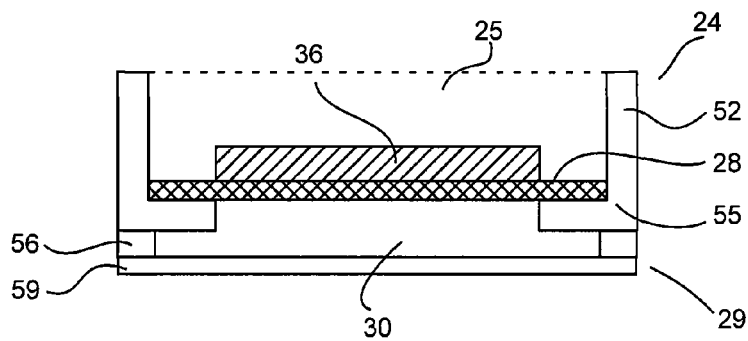
FIG. 18 is an exemplifying embodiment of an apparatus according to the present invention in the form of a petri dish having a film bottom that does not extend over the entire bottom area.

FIG. 18 is an exemplifying embodiment of an apparatus 2 according to the present invention in the form of a petri dish having a bottom portion formed by layer 28 that does not extend over the entire bottom area. First element 24 includes cylindrical wall 52 forming the wall of a petri dish and an outer annular portion 55 forming a circumferential portion of the bottom of the petri dish.

In conclusion, be it noted that the exemplifying embodiments discussed above serve merely to describe the teaching claimed, but do not limit it to the exemplifying embodiments.

What is claimed is:

1. An apparatus for receiving biological specimens, the apparatus being introducible into a laser microdissection device for laser microdissection of a biological specimen, the apparatus comprising:
a first element including a first opening extending from a first side to a second side of the first element;
a second element including a second opening extending from a third side to a fourth side of the second element, the second opening being closed at the third side, the second element being disposed relative to the first element so that the first opening is aligned with the second opening;
a laser-light-absorbing layer disposed between the first and second elements so as to seal, to liquids and gases, the first opening at the second side of the first element, the laser-light-absorbing layer being configured to support the biological specimen thereon and being capable of being cut through by laser light in a laser microdissection operation so that a portion of the biological specimen is receivable in the second opening so as to remain inside the apparatus; and at least one further element attached to the second element at the third side, wherein the third side faces away from the element, and wherein the further element has a substantially same design as a design of the second element.

2. The apparatus as recited in claim 1 wherein:
the first element has a form of a rectangular or round plate defining the first and second sides, the first and second sides being parallel to one another; and
the first opening has a rectangular or round configuration.

3. The apparatus as recited in claim 1 wherein at least one of the first element and the second element does not include an autofluorescent material.

4. The apparatus as recited in claim 1 wherein the second element is removably attached to the first element.

5. The apparatus as recited in claim 1 wherein the second element is removably attached to the first element using at least one of a snap-in and a fastening device.

6. The apparatus as recited in claim 1 wherein the at least one further element is at least one of removably and sealingly attached to the second element.

7. The apparatus as recited in claim 1 further comprising at least one of a cell culture medium, a nutrient medium and a liquid disposed in at least one opening of the first and second openings.

8. The apparatus as recited in claim 1 wherein the first element has a form of a petri dish, the layer forming a bottom of the petri dish.

9. The apparatus as recited in claim 1 wherein the layer is configured to receive the biological specimen on a region of the layer facing away from the second element.

10. The apparatus as recited in claim 9 wherein:
the apparatus is introducible into the laser microdissection device so that the second element is disposed below the first element;
the portion of the biological specimen is a microdissected portion; and
the microdissected portion is conveyable via gravity from the region of the layer facing away from the second element into the second opening.

11. The apparatus as recited in claim 9 wherein:
the apparatus is introducible into the laser microdissection device so that the second element is disposed below the first element;
the portion of the at least one biological specimen is a microdissected portion; and
the microdissected portion is conveyable, via laser pressure catapulting, from the region of the layer facing away from the second element into the second opening.

12. The apparatus as recited in claim 1 wherein:
the second element includes a closing region closing off the second opening; and
at least one of the layer and the closing region including a polymer film.

13. The apparatus as recited in claim 12 wherein the polymer film includes at least one of polyethylene naphthalate, polyethylene terephthalate, and polyethylene.

14. The apparatus as recited in claim 12 wherein at least one of the layer and the film is at least one of welded and adhesively bonded to at least one of the first and second element.

15. The apparatus as recited in claim 1 wherein at least one of the first element and the second element includes an optically transparent material.

16. The apparatus as recited in claim 15 wherein the optically transparent material includes at least one of glass, plastic and particular polycarbonate.

17. The apparatus as recited in claim 1 further comprising a cover configured to close off the first opening from an environment.

18. The apparatus as recited in claim 17 wherein the cover does not include an autofluorescent material.

19. The apparatus as recited in claim 17 wherein the cover is removable.

20. The apparatus as recited in claim 19 wherein the cover is configured to cooperate with the first element so as to provide a sterile closing off of the first opening.

21. The apparatus as recited in claim 17 wherein the cover includes an optically transparent material.

22. The apparatus as recited in claim 21 wherein the optically transparent material includes at least one of glass, plastic and particular polycarbonate.

23. The apparatus as recited in claim 1 wherein:
the second element has a form of a rectangular or round plate defining the third and fourth sides, the third and fourth sides being parallel to one another; and
the second opening has a rectangular or round configuration.

24. The apparatus as recited in claim 23 wherein:
the first element includes a plurality of first openings;
the second element includes a plurality of second openings, the second element including at least one of a multititration plate, a multi-well plate, and a microslide having the plurality of second openings; and
the second element is disposed relative to the first element so that each of the first openings is aligned with a respective one of the second openings.

25. The apparatus as recited in claim 23 wherein the second element includes a base closing off the second opening at the third side, the third side being opposite the fourth side.

26. The apparatus as recited in claim 25 wherein the base includes a glass plate.

27. The apparatus as recited in claim 25 wherein the base is unitary with the rest of the second element.

28. The apparatus as recited in claim 25 wherein the base has a thickness of less than 0.5 mm.

29. The apparatus as recited in claim 25 wherein the second element includes at least one of a multititration plate, a multi-well plate, and a microslide having the second opening.

30. The apparatus as recited in claim 23 wherein the second element includes a film disposed at the third side so as to close off the second opening, the third side being opposite the fourth side.

31. The apparatus as recited in claim 30 further comprising at least one further element attached to the second element at the third side, wherein the third side faces away from the first element, and wherein the further element has a substantially same design as a design of the second element.

32. The apparatus as recited in claim 31 wherein the at least one further element is at least one of removably and sealingly attached to the second element.

33. The apparatus as recited in claim 1 further comprising an environmental conditioning device configured to provide an environmental condition necessary for survival of the biological specimen, wherein the biological specimen includes a living biological specimen.

34. The apparatus as recited in claim 33 wherein the environmental conditioning device includes a device configured at least to maintain the apparatus at a definable temperature and/or to achieve a definable atmospheric composition around the biological specimen.

35. The apparatus as recited in claim 34 wherein the definable atmospheric composition includes a definably settable ratio of oxygen and nitrogen.

* * * * *